United States Patent
Tsubouchi et al.

(10) Patent No.: US 6,719,985 B1
(45) Date of Patent: Apr. 13, 2004

(54) COSMETIC MATERIAL CONTAINING CRYSTALLINE SUPERFINE SILK POWDER

(75) Inventors: Kozo Tsubouchi, Ibaraki (JP); Shoko Fujiura, Osaka (JP)

(73) Assignees: National Institute of Agrobiological Sciences, Tsukuba (JP); Eaudeleman Co., Ltd., Osaka (JP)

( * ) Notice: Subject to any disclaimer, the term of this patent is extended or adjusted under 35 U.S.C. 154(b) by 0 days.

(21) Appl. No.: 09/762,372

(22) PCT Filed: Mar. 1, 2000

(86) PCT No.: PCT/JP00/01191

§ 371 (c)(1),
(2), (4) Date: Feb. 2, 2001

(87) PCT Pub. No.: WO01/03654

PCT Pub. Date: Jan. 18, 2001

(30) Foreign Application Priority Data

Jul. 12, 1999 (JP) ............................................. 11-198233

(51) Int. Cl.[7] .............................. A61K 6/00; A61K 9/00; A61K 9/14; A61K 7/06
(52) U.S. Cl. ...................... 424/401; 424/489; 424/70.1; 424/400
(58) Field of Search ................................. 424/401, 489, 424/490, 491, 64, 63, 70.1, 400

(56) References Cited

U.S. PATENT DOCUMENTS 4,233,212 A * 11/1980 Otoi et al. ............... 260/123.7
4,325,741 A * 4/1982 Otoi et al. ..................... 106/38
5,853,764 A * 12/1998 Tsubouchi ................... 424/499

FOREIGN PATENT DOCUMENTS

JP 2615440 * 8/1996

\* cited by examiner

*Primary Examiner*—Thurman K. Page
*Assistant Examiner*—Humera N. Sheikh
(74) *Attorney, Agent, or Firm*—Flynn, Thiel, Boutell & Tanis, P. C.

(57) ABSTRACT

The invention provides a cosmetic material containing a crystalline superfine silk powder that has the original structure of silk yarn, properties such as an unique gloss, feeling of touch, flexibility, and elasticity; and various properties such as excellent coating power, spreadability, adhesion, feeling of touch, and formability, which are required of an extender powder or color material of cosmetics. The cosmetic material contains a colored crystalline superfine silk powder obtained by the steps of bringing a silk substance into contact with an alkali aqueous solution at temperatures ranging from 100° C. to 150° C. under a pressure ranging from 1 through 5 atmospheric pressures to weaken the silk substance to not greater than 0.02 g/d in tensile strength, dealkalizing and drying the silk substancepowdering the silk substance into a crystalline superfine silk powder below 3 μm in average particle diameter, and dyeing the crystalline superfine silk powder with a natural or synthetic color material, or mixing the crystalline superfine silk powder with a natural or synthetic color material.

12 Claims, 9 Drawing Sheets

Fig. 2

```
┌─────────────────────────────────────────────────────┐
│ Silk substance after alkali treatment, neutralization, │
│ washing in water, and drying                          │
└─────────────────────────────────────────────────────┘
                          ↓
┌─────────────────────────────────────────────────────┐
│ 1.  Mill (Frictional comminution)                    │
└─────────────────────────────────────────────────────┘
                          ↓
┌─────────────────────────────────────────────────────┐
│ 2.      Rotary impact pulverizer                     │
└─────────────────────────────────────────────────────┘
                          ↓
┌─────────────────────────────────────────────────────┐
│ 3.  Mill (Frictional comminution)                    │
└─────────────────────────────────────────────────────┘
                          ↓
┌─────────────────────────────────────────────────────┐
│ 4.      Air-jet pulverizer                           │
└─────────────────────────────────────────────────────┘
                          ↓
┌─────────────────────────────────────────────────────┐
│ 5.   Classification of particles                     │
└─────────────────────────────────────────────────────┘
                          ↓
┌─────────────────────────────────────────────────────┐
│          Superfine silk powder                       │
└─────────────────────────────────────────────────────┘
```

Fig. 4

| Silk substance after alkali treatment, neutralization, washing in water, and drying |

↓

| 1. Rotary impact pulverizer |

↓

| 2. Air-jet pulverizer |

↓

| fine silk powder |

Rupture test for supported beam made from silk power

Photographs showing formability of each powder
(kaolin, talc, mica, titanium and silk )

Kaolin

Talc

Mica

Titanium

Silk

Particle diameter of crystalline silk powder( μm)

COSMETIC MATERIAL CONTAINING CRYSTALLINE SUPERFINE SILK POWDER

TECHNICAL FIELD

The present invention relates to a cosmetic material that contains crystalline superfine silk powder below 3 μm in particle diameter and is suitable for application to the skin.

BACKGROUND TECHNOLOGY

Cosmetics include a variety of powders, for example, clay minerals (in the field of cosmetics, powdered clay minerals are referred to as "extender pigments") and/or color materials (for example, dyes and pigments).

Clay minerals include mainly talc, mica, kaolin, and sericite.

These powdered extender powders have been used for a long time because of their coating power, spreadability, adhesion, and the like, which are necessary for cosmetic materials.

Moreover, the extender powder is contained in the powder cosmetic material as a main ingredient. Taking talc as an example, which is a typical extender powder, it is contained in as high a proportion as 90% or more in talcum powder or baby powder, 80% in face rouge (compact type), around 50 to 80% in the facial powder or solid-type facial powder, and around 45% in eye shadow and cake-type foundations. Accordingly, the quality of the property of the extender powder becomes a decisive crucial factor in determining the quality of cosmetics.

Moreover, color materials for coloring cosmetic materials is divided into pigments and dyes: the pigment can be adsorbed by means of other substances whereas the dye can be adsorbed by means of other substances.

As a pigment, natural minerals such as tuff loam or loess, or powder color materials (inorganic pigments) of metallic oxides such as iron oxide, titanium oxide, zinc oxide, magnesium oxide, aluminum oxide, zirconium oxide, and chromium oxide have been conventionally used.

In the case of using cosmetics that contain these extender powders or color materials, particularly, a powder cosmetic material having a high content of an extender powder, complaints include drawbacks of unsuitability to the skin due to the powdery property.

Such an attempt as to make the content of the extender powder as low as possible to overcome this drawback would present a problem in that the feeling of touch would be degraded and solidified substances would become readily breakable because of the lack of balance between the powders.

Furthermore, the extender powder including talc, mica, kaolin, and sericite has coating power, spreadability, adhesion and the like to the skin surface. However, it absorbs moisture or lipids from the skin and causes the skin to seize due to dehydration, lipid removal, drying or the like. Its spreadability and adhesion cannot be said to be satisfactory.

On the other hand, coloring materials of natural minerals such as tuff loam or loess, and metallic oxide powders such as iron oxide, titanium oxide, zinc oxide, magnesium oxide, aluminum oxide, zirconium oxide, and chromium oxide are useful as raw materials. However, they have no function of absorption and desorption of moisture, and no permeability of moisture, so that they cannot be said to be a material suitable for skin since they would prevent respiration of the skin when brought into intimate contact with the skin.

Moreover, the color of cosmetic materials is prepared with difficulty by one type of color material and thus several types of color materials have been mixed for preparation.

In order to solve these extender powder or color material drawbacks, a technique has been suggested for use in coating the surface of powders such as talc, kaolin, titanium oxide, zinc oxide or the like with reproduced fibroin that has excellent affinity to skin and is a material suitable for a living body with good absorption and desorption of moisture. (Refer to Japanese Patent Publication No. Sho 28-250, Japanese Patent Publication No. Sho 57-11577, Japanese Laid-Open Patent Publication No. Hei 9-25217, Japanese Laid-Open Patent Publication No. Hei 9-309816, and Japanese Laid-Open Patent Publication No. Hei 9-302261).

In contrast to the development of a technique for such cosmetics which employs powders with color materials predominantly composed of an extender powder or a metallic oxide, which are predominantly composed of these clay minerals, coated with reproduced fibroin, research has been carried out for a long time in attempts to use a silk substance singly as a cosmetic powder.

For example, the invention according to Japanese Patent Publication No. Sho 26-4947 employs a silk powder as a cosmetic base material, the silk powder being obtained by spraying a reproduced fibroin aqueous solution in the atmosphere.

However, a reproduced silk powder, such as the silk powder according to the aforementioned invention, which is obtained from an aqueous solution into which silk yarn is dissolved has low crystallinity, that is, the reproduced silk powder is an amorphous silk powder.

The amorphous silk is soluble in water. Accordingly, when such an amorphous silk powder is adhered to skin moist with perspiration, the amorphous silk powder absorbs the perspiration to partly dissolve and become viscous.

When this is touched by hand, the silk powder lumps (particles) to become rough to the touch and provides a bad appearance.

Skin moist with perspiration occurs daily, such as after playing sports, taking a bath, during the rainy season or in sultry summer weather. In cases where powder cosmetic materials are used under this skin condition, it can be naturally understood that powder cosmetic materials containing amorphous silk powder are not suitable.

Accordingly, amorphous silk powder can be used when it is in a liquid state, that is, it can be used as a cosmetic material such as a lotion and can be used in a solid state (powder) with difficulty. In the case of using amorphous silk as in a powder, its content is around 5% or less.

Thereafter, such a technique was developed as attempting to expand the range of applications of the silk powder as a cosmetic raw material by increasing the crystallinity of the amorphous reproduced silk powder, that is, by decreasing the degree of solubility in water. An example includes a fine reformed silk powder and the method for manufacturing thereof (Japanese Laid-Open Patent Publication No. Hei 4-337331), the fine reformed silk powder being provided with the crystallinity of reproduced silk powder increased up to half that of silk yarn.

Other methods include one in which a silk powder obtained by powdering the silk yarn mechanically or physically is used as a cosmetic raw material.

For example, Japanese Patent Publication No. Sho 27-3650 provides a fine silk powder for use as a cosmetic material that is obtained through treatment of the silk yarn with an alkali aqueous solution, neutralization, washing in water, dehydration, drying, and powdering, with the diameter of the particles small enough to pass through a mesh of No.300 (10 μm in particle diameter).

Moreover, a method is suggested in which the silk yarn is heated with saturated vapor or heated vapor, then the silk is released to expand under low pressure, and then dried to be powdered in order to obtain a silk powder 30 to 50 μm in diameter (refer to Japanese Patent Publication No. Sho 61-36840 and Japanese Patent Publication No. Sho 63-51160). Another method is suggested in which the silk yarn is dissolved in a certain aqueous solution, then the aqueous solution is dialyzed to obtain a silk fibroin aqueous solution which is in turn brought into contact with a coagulating liquid, and then the precipitated fine particulate silk fibroin is dried to obtain a silk powder of 6.5 to 19 μm in diameter (refer to Japanese Laid-Open Patent Publication No. Hei 4-88027). Another method is suggested in which the silk fibroin is powdered in a multi-stage process where dry and mechanical powdering means are employed, and is subjected to β treatment at least in one stage of the multi-stage process or after the multi-stage process to obtain a superfine silk fibroin powder 3.25 μm in average particle diameter. (Refer to Japanese Laid-Open Patent Publication No. Hei 6-339924.)

The present applicants have already suggested a method in which a silk substance is brought into contact with an aqueous solution of an alkali metal compound under an atmospheric pressure at a temperature of 95° C. or more to allow the substance to be weakened in strength, then the resulting silk substance is dealkalized and dried, and the silk substance is powdered to obtain a crystalline superfine silk fibroin powder 3 to 6 μm in average particle diameter (Japanese Laid-Open Patent Publication No. Hei 8-198970, Patent No. 2615440).

In the aforementioned prior arts, powders such as talc, kaolin, titanium oxide, and zinc oxide, which are coated with the reproduced fibroin, can provide a certain effect on solving these problems. However, their cores themselves are made up of a metallic oxide and do not essentially make improvements in moisture and air permeability.

Moreover, the prior arts have a drawback in presenting a problem that the fibroin coating in use, which absorbs body fluids such as sweat, is stripped off from the metal oxide core and thus the surface of the metal oxide is apt to be exposed. Accordingly, they do not provide means for essentially solving the problems.

On the other hand, in the prior art that employs the silk powder as a cosmetic raw material, such a silk powder has been developed as a coarse powder several tens of μm in average particle diameter to a fine powder 3 μm in average particle diameter.

However, powders around 10 μm in diameter or more lack the smooth feeling of touch or the feeling of suitability. In addition, powders below 10 μm and above 3 μm in diameter provide improved feelings of touch and fitness, however, they are not yet satisfactory in this point and still not sufficient in terms of formability (stability of particles).

The object of the present invention is to provide a cosmetic material containing a crystalline superfine silk powder that is provided with the original structure of silk yarn; with properties such as its unique gloss, feeling of touch, flexibility, and elasticity; and with various properties such as excellent coating power, spreadability, adhesion, feeling of touch, and formability, which are required of the extender powder or color material of cosmetics.

Another object of the present invention is to provide a cosmetic material in which part of or all of the extender powder or color material which has been used in conventional cosmetics, is replaced by the crystalline superfine silk powder that is provided with the aforementioned original structure of silk yarn; with properties such as its unique gloss, feeling of touch, flexibility, and elasticity; and with various properties such as excellent coating power, spreadability, adhesion, feeling of touch, and dye-affinity by means of a pigment, which are required of the extender powder or color material of cosmetics.

Another object of the present invention is to provide a cosmetic material containing the coloring crystalline superfine silk powder that is provided with functions as an extender powder or a color material.

DISCLOSURE OF THE INVENTION

In order to achieve the aforementioned objects, the present invention employs technical items as requirements as shown below.

That is, the present invention lies in:

(1) A cosmetic material containing a crystalline superfine silk powder obtained in the steps of bringing a silk substance into contact with an alkali aqueous solution at a temperature of 100° C. or more under one atmospheric pressure or more to weaken the silk substance in strength; thereafter, dealkalizing and drying the silk substance; and then, powdering the silk substance into powder below 3 μm in average particle diameter, (2) A cosmetic material containing clay minerals and/or a color material, wherein
part of or all of said clay mineral and/or a color material are replaced by a crystalline superfine silk powder obtained in the steps of bringing a silk substance into contact with an alkali aqueous solution at a temperature of 100° C. or more under one atmospheric pressure or more to weaken the silk substance in strength; thereafter, dealkalizing and drying the silk substance; and then, powdering the silk substance into powder below 3 μm in average particle diameter, (3) A cosmetic material containing a crystalline superfine silk powder obtained in the steps of bringing a silk substance into contact with an alkali aqueous solution at temperatures ranging from 100° C. to 150° C. under a pressure ranging from 1 through 5 atmospheric pressures to weaken the silk substance to not greater than 0.02 g/d in tensile strength; thereafter, dealkalizing and drying the silk substance; and then, powdering the silk substance into powder below 3 μm in average particle diameter, (4) A cosmetic material according to aforementioned (1), (2), or (3), wherein when the silk substance is powdered, an impact powdering and a frictional powdering are combined to powder the silk substance into a crystalline superfine silk powder below 3 μm in average particle diameter, (5) A cosmetic material according to aforementioned (1), (2), (3), or (4), wherein when the silk substance is powdered, an impact powdering and a frictional powdering are combined to powder the silk substance, which is then classified into a crystalline superfine silk powder below 3 μm in average particle diameter, (6) A cosmetic material according to aforementioned (5), wherein when powdering is carried out by a combination of the impact powdering and the frictional powdering, a dried silk substance is powdered into a silk powder 4 to 15 μm in average particle diameter through the impact powdering—the frictional powdering and the frictional powdering—the impact powdering, or the frictional powdering—the impact powdering—the frictional powdering being in sequence, and then the impact powdering is carried out to obtain a crystalline superfine silk powder belw 3 μm in average particle diameter, (7) A cosmetic material containing a colored crystalline superfine silk powder obtianed by the steps of bringing a silk substance into contact with an alkali aqueous solution at a temperature of 100° C. or more under one atmospheric pressure or more to weaken the silk substance in strength; thereafter, dealkalizing and drying the silk substance; then, powdering a resulting dried silk substance into a crystalline superfine silk powder below 3 μm in average particle diameter; and thereafter, dyeing said crystalline superfine silk powder with a natural or synthetic color material, or mixing said crystalline superfine silk powder with a natural or synthetic color material, (8) A cosmetic material containing clay minerals and/or a color material, wherein
part of or all of said extender powder and/or a color material are replaced by a colored crystalline superfine silk powder obtained in the steps of bringing a silk substance into contact with an alkali aqueous solution at a temperature of 100° C. or more under one atmospheric pressure or more to weaken the silk substance in strength; thereafter, dealkalizing and drying the silk substance; then, powdering the silk substance into a crystalline superfine silk powder below 3 μm in average particle diameter; and thereafter, dyeing said crystalline superfine silk powder with a natural or synthetic color material, or mixing said crystalline superfine silk powder with a natural or synthetic color material, (9) A cosmetic material containing a colored crystalline superfine silk powder obtained by the steps of bringing a silk substance into contact with an alkali aqueous solution at temperatures ranging from 100° C. to 150° C. under a pressure ranging from 1 through 5 atmospheric pressures to weaken the silk substance to not greater than 0.02 g/d in tensile strength; thereafter, dealkalizing and drying the silk substance; then, powdering the silk substance into a crystalline superfine silk powder below 3 μm in average particle diameter; and thereafter, dyeing said crystalline superfine silk powder with a natural or synthetic color material, or mixing said crystalline superfine silk powder with a natural or synthetic color material, and

(10) A cosmetic material containing a crystalline superfine silk powder obtained by the steps of bringing a silk substance into contact with an alkali aqueous solution at temperatures ranging from 100° C. to 150° C. under a pressure ranging from 1 through 5 atmospheric pressures to weaken the silk substance to not greater than 0.02 g/d in tensile strength; thereafter, dealkalizing and washing the silk substance in water; then, dyeing the silk substance with a natural or synthetic color material; and then, powdering the silk substance into a crystalline superfine silk powder below 3 μm in average particle diameter.

Production of Crystalline Superfine Silk Powder:

According to the present invention, in order to obtain crystalline superfine silk powder below 3 μm in average particle diameter, the following configuration is employed. That is, 1) a raw material of a silk substance such as cocoon filaments, silk yarn, and raw silk
2) is brought into contact with an alkali aqueous solution,
3) at temperatures ranging from 100° C. to 150° C.,
4) under pressure ranging from 1 through 5 atmospheric pressures,
5) to weaken the silk substance to around 0.02 g/d or less in tensile strength,
6) thereafter, the resulting silk substance is dealkalized and dried, and
7) then, the resulting dried silk substance is powdered.

In the present invention, it is important to treat the silk substance so that the tensile strength thereof is reduced to around 0.02 g/d or less. It is difficult to obtain powder below 3 μm in average particle diameter with a tensile strength above 0.02 g/d.

Moreover, it is important to treat the silk substance at a temperature of 100° C. to 150° C. and under a pressure so as to provide uniform degradation in strength.

Moreover, it is desirable to employ, in the powdering process, a multi-stage powdering method in two stages or more in which the impact powdering and frictional powdering are combined together.

The silk substance for use in the present invention includes cocoon filaments, raw silk, silk yarn (yarn from which sericin is excluded by degumming), and lint such as leftover thereof.

Moreover, the silk substance can employ woven fabrics, knit fabrics, non-woven fabrics, net yarn, and the like, which are formed of these respective yarns.

The silk substance can employ one or more selected from them.

In order to implement the present invention, the silk substance is first treated by being brought into contact with an alkali aqueous solution at a temperature above 100° C., preferably, at a temperature within a range of 120° C.±10° C. and under a pressure.

As an alkaline substance in the alkaline aqueous solution, sodium carbonate, sodium hydrogen-carbonate, potassium carbonate, sodium hydroxide, potassium hydroxide may be used individually or mixed for use.

The degree of alkalinity of the alkaline aqueous solution (alkalinity) is a pH of 9 to 12.5, preferably, a pH of 10.5 to 12.0.

With a pH of less than 9, the strength cannot be reduced uniformly and efficiently, while with a pH above 12.5, an excessive dissolved portion of the silk yarn or the like reduces the rate of collection.

Sodium carbonate, an alkaline substance, has a buffering action as an aqueous solution and an increase in concentration would hardly cause the pH thereof to increase up to the order of 12 or more.

However, a trace amount of mixture of sodium hydroxide into sodium carbonate may cause the total amount of alkaline substance used to decrease.

The silk substance in the alkali aqueous solution is treated by soaking the silk substance in the alkaline aqueous solution of a temperature above 100° C.

The time for the silk substance to be in contact with the alkaline aqueous solution (alkali treatment time) is a time necessary to allow the strength of the silk substance to uniformly decrease to a degree suitable for forming a superfine powder regardless of whether it is domestic silk or wild silk.

For example, a silk substance is kept in contact with the alkaline aqueous solution until the tensile strength thereof becomes around 0.02 g/d or less and more preferably, up to such an extent that the strength of the silk yarn is substantially immeasurable in the tensile test (0.01 g/d or less), that is, until the silk yarn loses a form thereof available for measurement.

In general, the treatment time is 0.5 to 5 hours. In cases where silk yarn has yarn fabrics large in diameter or has sericin adhesion found thereon or in cases where the strength cannot be readily decreased such as in the case of wild silk yarn, two to three hours or more need to be added or the concentration of the alkaline substance needs to be increased.

A specific time required for alkali treatment can be determined by examining the relationship between the ease of powdering the silk substance whose strength has been reduced through the alkali treatment, the time for contact with the alkali, and the temperature.

What is important to reducing the strength of the silk substance through the alkali treatment is to allow the strength of the silk substance to decrease uniformly.

In this case, what is particularly essential is that if the silk substance to be subjected to the alkali treatment is well separated, powder below 3 $\mu$m in average particle diameter may be obtained even by boiling (under an atmospheric pressure) at a temperature around 100° C. of the alkali treatment. However, this case will result in a variation in strength and lead to a prolonged alkali treatment time, requiring a greater amount of alkaline substance and thus providing a ratio of collection significantly reduced.

Therefore, it is important to weaken variations in strength after the alkali treatment irrespective of the portions of the silk substance such as cocoon filaments and silk yarn.

The present invention overcomes this problem by performing the alkali treatment under a pressure above the atmospheric pressure.

A pressure above the atmospheric pressure can be obtained by putting the silk substance, an alkali substance, and water into a sealed container and then by increasing the temperature thereof to a temperature greater than the boiling temperature. The pressure ranges substantially from 1 through 5 atmosphere. A pressure ranging from 1 through 3 atmospheres may be preferably employed in practice particularly in industrial production.

For example, the alkali treatment for the silk substance would be carried out more uniformly under a pressure of 0.01 atmosphere added to atmospheric pressure than under atmospheric pressure and provide a finer average particle diameter. However, it is far more effective to preferably carry out the alkali treatment under more than 0.1 atmosphere added to the atmospheric pressure and more preferably under two atmospheres, at a temperature of 120° C.±10° C.

The silk substance after having been subjected to the alkali treatment is separated from the alkaline aqueous solution, thereafter alkaline substances adhered thereto are removed by washing in water to be dealkalized, and then the silk substance is dried.

Neutralization (pH7±1) or making the silk substance slightly acidic (pH5±1) with acids such as hydrochloric acid or tartaric acid will be effective for the dealkalization.

Moreover, the addition of natural acids (such as a liquid squeezed out of a citrus, for example, lemon) after neutralization and washing in water would allow the silk substance to effectively suit the skin and thus would make the substance more suitable for a powder raw material for use in cosmetics.

Drying is preferably carried out using a dryer for positive drying, however, natural drying should be also possible.

Subsequently, the powdering of the resulting silk substance is carried out.

The superfine powdering of the silk substance is carried out by means of combining an impact powdering (coarse powdering and superfine powdering) with frictional powdering (grinding).

For example, any of the multi-stage powdering methods in a) through c) below are employed.
  a) impact powdering (coarse powdering)→grinding→impact powdering (superfine powdering)→(particle size classification)
  b) grinding→impact powdering (coarse powdering)→impact powdering (superfine powdering)→(particle size classification)
  c) grinding→impact powdering (coarse powdering)→grinding→impact powdering (superfine powdering)→(particle size classification)

Particles are preferably powdered into 4 to 15 $\mu$m in average particle diameter before the last impact powdering (superfine powdering) is carried out.

In the end, crystalline silk superfine powdered particles below 3 $\mu$m in average particle diameter are obtained by the superfine powdering.

Within this range of particle diameter, impact powdering (superfine powdering) is carried out with great efficiency.

In particular, powder below approximately 1 $\mu$m or less can be obtained by the classification of particle sizes of the resultant silk superfine powdered particles.

Furthermore, in order to obtain colored crystalline superfine silk powder, one of the methods can be selectively used: one for powdering after the silk substance having been subjected to the alkali treatment has been dyed with a natural or synthetic color material (such as a natural pigment, a synthetic pigment, a natural dye, or a synthetic dye); and the other for dyeing after powdering.

Pigments and dyes are apt to be fixed in an acid bath and therefore dyeing (after or before powdering the silk substance) with pigments or dyes is preferably carried out in an acid bath.

The resulting white or colored superfine silk powder provides an excellent sense of touch.

In addition, the superfine silk powder has the power of solidification and thus can be effectively used as a binder to increase the formability of a cosmetic raw material that has bad formability.

In particular, powder having a diameter of around 1 $\mu$m provides significantly improved adhesion to the skin and spreadability and serves as a skin protective material including raw materials for cosmetics and resin composites.

In cases where the material silk substance is brought into contact with the alkali aqueous solution to be treated under a pressure at a temperature of 100° C. to 150° C., the treatment is carried out by soaking the silk substance into an alkaline aqueous solution in a glass container or in a pressure-resistant metallic container made of stainless steel.

At this time, in order to weaken the strength of the material silk substance uniformly, fiber-shaped silk substances such as cocoon filaments, raw silk, or silk yarn are preferably separated as much as possible.

Dealkalization after the alkali treatment is carried out by repeating washing and dehydrating for neutralization of pH, or by neutralization (pH7±1) or making the silk substance slightly acidic (pH5±1) with acids such as hydrochloric acid or tartaric acid, and thereafter washing is repeated through washing in water and a dehydration process.

In the dehydration process, a cloth-shaped filter, for example, a filter with mesh so fine as to collect fine silk particles around 0.5 $\mu$m in particle diameter is used.

In the alkali treatment process, non-crystalline portions of the material silk substance dissolve gradually into the alkali aqueous solution and the dissolved silk substance is removed with water at the time of dehydration. Accordingly, the silk substance to be powdered is comprised of a crystalline silk substance in which the structure provided intrinsically for silk yarn remains (crystalline structure of a β-type with fibroin molecules uniaxially oriented).

In the alkali treatment under a pressure according to the present invention, the amount of an alkaline substance required is much less than that required in the case of the aforementioned U.S. Pat. No. 2,615,440 in which the alkali treatment is carried out under a normal pressure. For example, the ratio of silk to carbonic acid soda must be 1:1 in the case of Pat. No. 2,615,440, while the ratio of silk to carbonic acid soda is only 1:0.5 in the case of the present invention in which the alkali treatment is carried out under a pressure at a temperature of 120° C.

This means that an improved effect is provided, in industrial production of crystalline superfine silk powder, in which the number of times of washing in water and dehydration after the alkali treatment and the amount of acid required can be naturally reduced.

The silk substance has a property increasing the moisture absorption and water absorption while decreasing the crystallinity, and the silk becomes softened by absorbing moisture or water and is readily deformed.

When dried after the absorption of moisture or water, silk powder having such low crystallinity flocculates firmly into hard clusters becoming useless. Accordingly, the powder needs to be a crystalline powder in order to keep the unique property of silk. Therefore, it is desirable to employ a physical powdering method for producing the crystalline powder in industry.

On the other hand, as described above, the prior arts were limited to obtain powder on the order of 3 μm in average particle diameter even by applying physical powdering methods.

That is, any type of physical pulverizer provides powdered particles of a limited size that is determined by the property of the powered material so long as the same type of pulverizer is used. Thus, powder limitlessly small in diameter cannot be obtained.

In general, a pulverizer that provides a higher impact speed can produce powder of smaller diameters. However, the smaller the diameter of the powder particles, the lower the particle's kinetic energy becomes. This decreases the probability of exceeding the break speed of the particles at which stress is produced sufficient to break the particles. Accordingly, the energy efficiency of the pulverizer will decrease in an accelerated manner when the particles become smaller in diameter than a certain diameter.

Therefore, the average particle diameter that can be obtained by the conventional method, in which the silk substance is powdered to provide superfine powder, is considered to be limited to 3 μm.

The powdering method is largely divided into two methods: one for dissolving and thereafter solidifying the silk substance to be powdered; the other for physically powdering the silk substance.

In the case where the silk substance is dissolved and thereafter powdered, the structure provided intrinsically for silk does not remain (an uniaxially oriented β-type crystalline structure).

On the other hand, in the case where the silk yarn is physically powdered to form superfine silk powder, the structure provided intrinsically for silk yarn is left as it is, however, the amount of the structure to remain depends on the powdering method, which exerts an effect on the formability.

Manufacturing examples of crystalline superfine silk powder according to the present invention are shown below.

MANUFACTURING EXAMPLE 1

An Eri silkworm cocoon shell is boiled in a 0.5% sodium carbonate aqueous solution (bath ratio of 50 times) to remove sericin, and is then washed in water and dried to form Eri silkworm silk yarn.

This silk yarn (fibroin fibers) with the composition shown in Table 1 is put into a stainless steel container and is treated for 2 hours at a temperature of 120° C. (under a pressure of 2.02 atmospheres) with the container tightly closed.

Sodium hydrosulfite is a bleaching agent and Clewat is a trade name of the sequestering agent (made by The Teikoku Chemical Industry Co., Ltd.).

These agents exert an effect on the whiteness of Eri silkworm yarn after the alkali treatment, which are required depending on the material of the container used and do not particularly exert an effect on the powdering without using the agents.

The amount of sodium carbonate and the time of alkali treatment exert an effect on the powdering.

In the case of Table 1, the strength of the silk substance was reduced to around 0.01 g/d.

The alkali treatment method is shown in Table 1.

TABLE 1

| Eri silkworm silk yarn | 20 (g) |
|---|---|
| Sodium carbonate | 8 (g) |
| Seguestering agent (Clewat) | 5 (g) |
| Sodium hydrosulfite | 1 (g) |
| Water | 600 (g) |

The tensile strength was measured by means of a Tensilon UTM-II.

An alkali solution containing alkali-treated Eri silkworm silk yarn was reduced to 8.5 in pH with hydrochloric acid, then made slightly acidic (pH5±1) with tartaric acid, then put into a bag-shaped container of woven fabrics with a high degree of mesh, repeatedly washed in water and dehydrated four times, and then dried at around 40° C.

In the powdering treatment, an agitating crusher (a type by Ishikawa) was used for frictional powdering (or grinding) and then a rotary impact pulverizer (Sample Mill KI.-1 made by Fuji Denki Kogyo) was used for powdering to obtain fine silk powder of around 12 μm in an average particle diameter.

Moreover, this fine powder is crushed by means of an air-jet pulverizer (Current Jet CJ-10 made by Nisshin Flour Milling Co., Ltd.) and thereafter classified by means of a classifier (Turbo classifier TC-16N made by Nisshin Flour Milling Co., Ltd.). Thus, superfine powder was obtained which has average particle diameters of around 2.6 μm and 0.9 μm (FIG. 1).

As can be seen clearly in FIG. 1, particles 5 μm or more in diameter are contained among particles around 1 μm or less in an average particle diameter that are obtained through the powdering and classification processes.

This superfine powder can be combined into fabrics around 10 μm in fiber diameter to improve the property of the fabrics.

MANUFACTURING EXAMPLE 2

Bourette (by-product silkworm silk yarn not more than several twos of cm in the fiber length of the domestic silkworm yarn) produced in the silk spinning process was used as a raw material of the silk substance. With the composition shown in Table 2, the bourette was put into a glass bottle and treated for two hours at a temperature of 125° C. (under a pressure of 2.37 atmosphere) with the bottle tightly sealed.

TABLE 2

| | |
|---|---|
| Domestic silkworm silk yarn | 20 (g) |
| Sodium carbonate | 4.5 (g) |
| Clewat | 4 (g) |
| Sodium hydrosulfite | 2 (g) |
| Water | 400 (g) |

The treated silk substance was neutralized, washed in water, and dried, and thereafter powdered.

The substance was neutralized with hydrochloric acid to have a pH of 7±1, and then dehydrated and washed in water repeatedly four times, and finally dried at a temperature of 40° C.

The powdering treatment was carried out by means of the same pulverizer used in Manufacturing Example 1.

That is, in the powdering, the agitating crusher (a type by Ishikawa) was used for frictional powdering; then the rotary impact pulverizer (Sample Mill KI.-1 made by Fuji Denki Kogyo) was used for powdering; and then the agitating crusher (a type by Ishikawa) was used again for frictional powdering to obtain fine silk powder of around 11 $\mu$m in an average particle diameter.

This fine powder was crushed by means of the air-jet pulverizer (Current Jet CJ-10 made by Nisshin Flour Milling Co., Ltd.) to obtain powder of around 2.0 $\mu$m in an average particle diameter after the air-jet superfine powdering treatment.

The powder was classified thereafter to obtain crystalline superfine silk powder which has average particle diameters of around 2.5 $\mu$m and 0.9 $\mu$m.

FIG. 2 shows the powdering process by a flow diagram.

MANUFACTURING EXAMPLE 3

Raw silk of domestic silkworms was boiled for one hour for degumming in a 0.1% sodium carbonate aqueous solution 50 times greater in quantity than the raw silk to form fibroin fabrics (silk yarn).

This silk yarn was used as a material substance to perform an alkali treatment under the conditions shown in Table 3.

For the powdering process after the alkali treatment, case (1), case (2), and case (3) of Table 3 were carried out like in the processes shown in FIG. 2 excluding the classifying process; case (4) of Table 3 was carried out as in the process shown in FIG. 3; and case (5) of Table 3 as in the process shown in FIG. 4.

FIG. 3 and FIG. 4 show flow diagrams of the powdering process.

Table 3 shows the average particle diameter of the resultant powder and the ratio of powder collection.

In addition, classification of the resultant powder obtained in case (3) of Table 3 provided powder of 1.2 $\mu$m and 2.5 $\mu$m in an average particle diameter.

TABLE 3

| Condition | (1) | (2) | (3) | (4) | (5) |
|---|---|---|---|---|---|
| Treatment temperature (° C.) | 100 | 110 | 120 | 120 | 120 |
| Atmospheric pressure (atm) | 1.03 | 1.46 | 2.02 | 2.02 | 2.02 |
| Treatment time (h) | 8 | 5 | 2.5 | 2.5 | 2.5 |
| Sodium carbonate (g) | 20 | 10 | 4 | 4 | 4 |
| Domestic silkworm silk yarn (g) | 20 | 20 | 20 | 20 | 20 |
| Sodium hydrosulfite (g) | 1 | 1 | 1 | 1 | 1 |
| Water (g) | 500 | 500 | 500 | 500 | 500 |
| Average particle diameter ($\mu$m) | 2.8 | 2.1 | 1.8 | 2.3 | 3.2 |
| Ratio of powder collection (%) | 50 | 55 | 60 | 60 | 60 |

REFERENCE TEST EXAMPLE 1

Table 4 shows the relationship between the average particle diameter of the silk powder particles and the adhesion property thereof, concerning the silk powder of domestic silkworms which was obtained by the methods of Manufacturing Examples 2 and 3, and in the intermittent processes thereof.

An amount of around 10 g of silk powder with different average particle diameters is placed on a sheet of paper and is spread to about 50 cm$^2$. Then, a test piece is placed on the powder to be adhered thereto and further, the test piece was covered with an amount of 10 g of the powder of the same average particle diameters.

Subsequently, the test piece buried in the powder was lifted vertically with tweezers. Then, the test piece was weighed with the powder adhered thereto to calculate the amount of powder adhered to the surface and reverse side of the test piece per unit area.

The measurement was carried out in a room at a temperature of 20° C. with 65% RH.

The test piece had the shape of a film with a side thereof having an area of around 10 cm$^2$ (10 cm$^2$±0.5 cm$^2$).

Three types of materials of metal (aluminum), resin (polyethylene), and natural substance (silk fibroin) were used in the test piece.

As can be seen clearly in Table 4, over a range of average particle diameters around 3 $\mu$m or less, the smaller the particles diameter, the larger the amount of powder adhered to the test piece for any material.

TABLE 4

Relationship between average particle diameter and adhesion property of silk powder particles

| Average particle diameter ($\mu$m) | Amount of powder adhered to the test piece (mg/cm$^2$) | | |
|---|---|---|---|
| | Silk fibroin | Polyethylene | Aluminum |
| 0.9 | 3.003 | 0.863 | 1.418 |
| 1.21 | 2.887 | 0.761 | 1.233 |
| 2.32 | 1.390 | 0.589 | 1.045 |
| 2.57 | 1.148 | 0.520 | 0.904 |
| 3.65 | 0.613 | 0.311 | 0.566 |
| 5.40 | 0.452 | 0.297 | 0.491 |
| 12.20 | 0.304 | 0.206 | 0.281 |

REFERENCE TEST EXAMPLE 2

Using the silk powder obtained by the methods of Manufacturing Examples 1 through 3, the sense of touch thereof was evaluated in a panel experiment by five adult women.

The test was carried out in a room of constant temperature and constant humidity at 20° C. with 65% RH. An amount of 1 g of silk powder was placed on the inside of the forearm of one arm and was pressed with the other hand to be rubbed in various directions. The subjects were asked to fill in a questionnaire of how they felt at that time.

The results are shown in Table 5.

As shown in Table 5, it can be seen that improved adhesion to the skin, spreadability, and smoothness are provided by the silk powder below 3 μm in an average particle diameter, particularly by that below 1 μm in diameter.

TABLE 5

| Particle diameter (μm) | Sense of touch |
| --- | --- |
| 12 | Rough feeling |
| 8 | Not rough to touch |
| 5 | Soft to touch |
| 3.7 | Soft to touch |
| 2.3 | Very soft to touch, good in adhesion to the skin, and good in spreadability on the skin |
| 0.9 | Very soft to touch, very good in adhesion to the skin, and very good in spreadability on the skin |

On the Manufacturing of Colored Crystalline Superfine Silk Powder

The crystalline superfine silk powder is colored and used as cosmetic materials. Here, the manufacturing of this colored crystalline superfine silk powder is described below.

The crystalline superfine silk powder, according to the present invention, has a good dyeing property and is dyed with synthetic color materials such as natural pigments, synthetic pigments, natural dyes, synthetic dyes (such as direct dyes, acid dyes, basic pigments, and reactive dyes), or mixed with these color materials. The crystalline superfine silk powder is thereby dyed or colored into a variety of colors to be used as colored crystalline superfine silk powder.

In particular, the crystalline superfine silk powder is an extremely good cosmetic raw material that can be dyed throughout said powder even with pigments.

This colored crystalline superfine silk powder also functions as an extender powder and a color material. Accordingly, when so colored as to have a desired color, the powder requires no other pigments such as color materials and thus serves as a very useful cosmetic raw material.

Color materials for coloring include known color materials that are conventionally used for dyeing silk as a matter of course, as well as plant color materials such as curcuma, jasmine, carthamus, phellodendron amurense, madder, or paprika, a color material such as cochineal that is extracted from insects, and a color material such as shell purple that can be extracted from shells.

The color materials further include a color material extracted from color cocoons such as domestic yellow cocoons, blue white cocoons, red cocoons, and bamboo-leaf-color cocoons. The green or blue of wild silkworm cocoons and rhodinia fugax silkworm cocoons and the gold color of cricula silkworm cocoons can also be used as a color material.

Manufacturing of Cosmetic Materials:

The crystalline superfine silk powder, according to the present invention, is a crystalline superfine silk powder, below 3 μm in an average particle diameter, that is provided with the original structure of silk yarn; with properties such as a unique gloss, feeling of touch, flexibility, and elasticity; and with various properties such as good coating power, spreadability, adhesion, feeling of touch, and formability, which are required of cosmetics.

Therefore, in a conventional cosmetic material containing an extender powder and/or a color material such as talc, mica, kaolin, or sericite, part of or all of the extender powder and/or color material can be replaced with the aforementioned crystalline superfine silk powder below 3 μm in an average particle diameter according to the present invention.

The cosmetic materials, according to the present invention, include those predominantly composed of the aforementioned crystalline superfine silk powder below 3 μm in an average particle diameter, more specifically, such powdery cosmetics like facial powder or solid-type facial powder, and face rouge composed of an oil agent (bonding agent) or a color material, eye shadows, and foundations (such as a cake type foundation, a powdery foundation, an oil foundation, a stick foundation, and a liquid foundation).

The ratio of mixture of the crystalline superfine silk powder in a cosmetic material (by weight) is 1 to 100% in a powdery material, preferably, 40 to 100%.

A cosmetic material like a lipstick composed of an oil agent (binder) has ratios from 1 to 70%, preferably, 1 to 40%.

A stick-shaped cosmetic material like a lipstick exceeding the ratio of 70% is easily broken.

As described above, according to the present invention, the crystalline superfine silk powder below 3 μm in an average particle diameter is contained in a cosmetic material to form a cosmetic raw material that is provided with the original structure of silk (an uniaxially oriented β-type crystalline structure); with properties such as an unique gloss, feeling of touch, flexibility, and elasticity; and with various properties such as good coating power, spreadability, adhesion, feeling of touch, and formability, which are required of an extender powder of cosmetic materials.

Furthermore, said crystalline superfine silk powder can be colored with a variety of color materials into various colors, and serves as a color material as well.

In particular, the crystalline superfine silk powder can be dyed throughout with pigments, providing clear colors.

BRIEF DESCRIPTION OF THE DRAWINGS

FIG. 2 is a flow diagram showing a powdering process after an alkali treatment.

FIG. 4 is a flow diagram showing a powdering process after an alkali treatment.

BEST MODE FOR CARRYING OUT THE INVENTION

Figure 1:
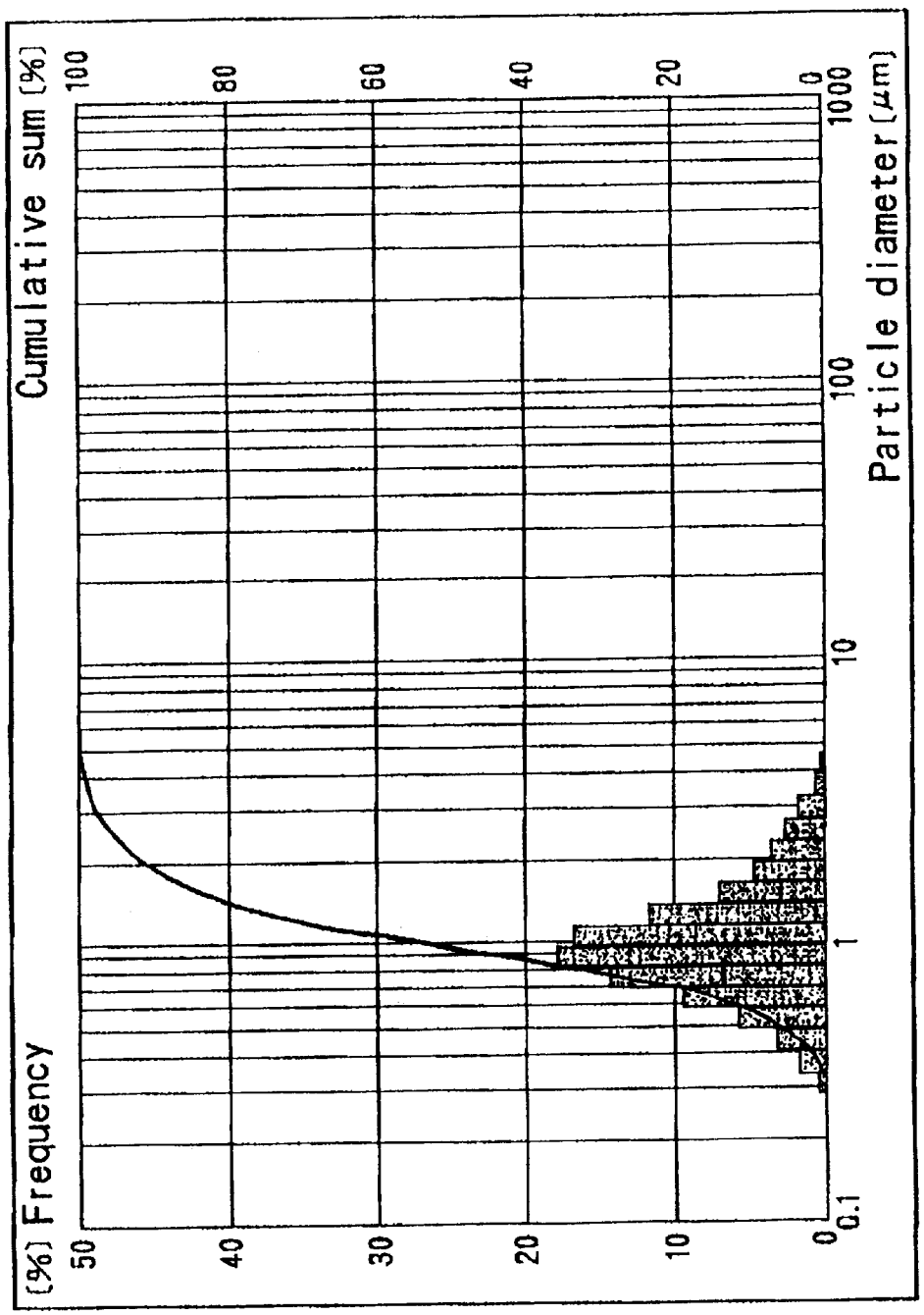
FIG. 1 is a view showing a distribution of particle sizes of superfine powder about 0.9 μm in an average particle diameter in Manufacturing Example 1.
Figure 3:
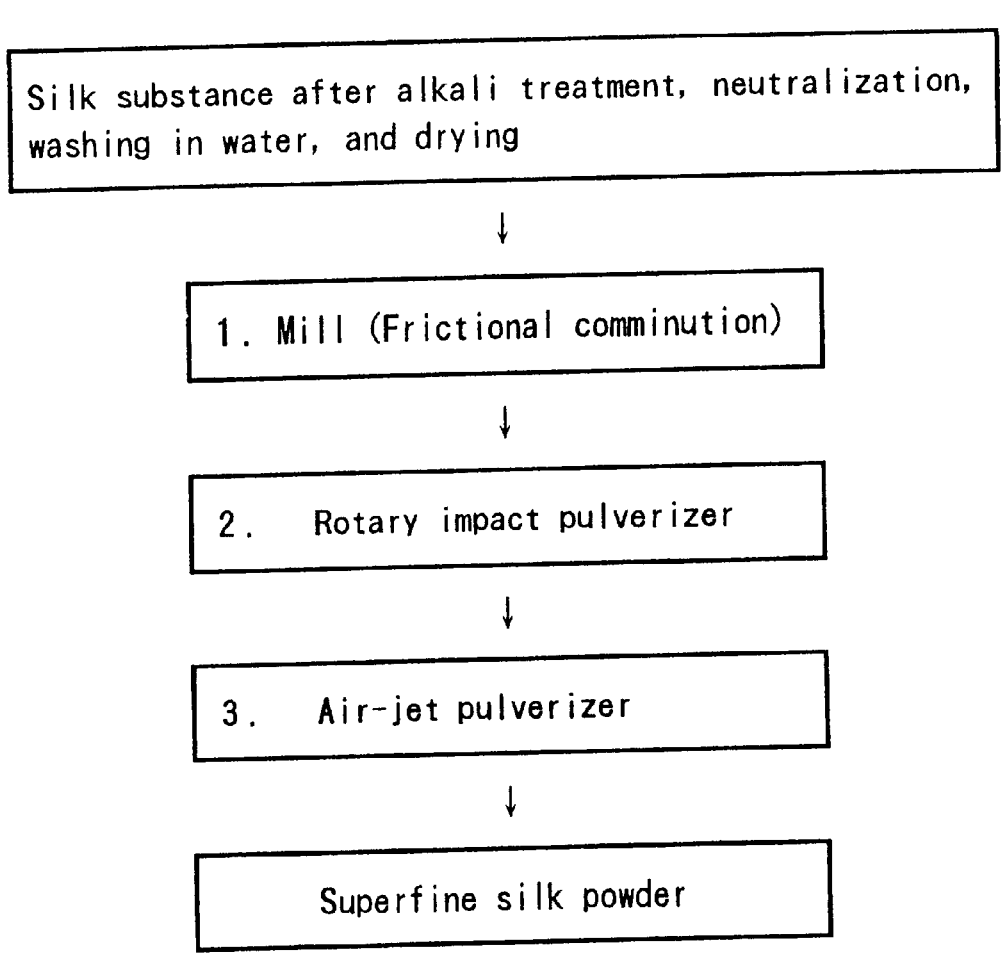
FIG. 3 is a flow diagram showing a powdering process after an alkali treatment.

The embodiments of the present invention have been described above. Now, the examples (1 through 7) are to be shown below.

Moreover, the present invention is not limited to only the following examples.

EXAMPLE 1

A patch test for crystalline superfine silk powder and talc powder (skin irritation)

Talc JA-46R was used as the talc powder.

The crystalline superfine silk powder obtained in Manufacturing Example 1 was used as the silk powder.

Test: With the silk and talc powder employed as specimens, the Finn-chamber was used for 20 adults (10 males and 10 females) ages 24 through 59 to affix a silk powder and talc powder to the inside portion of the arm. The skin reaction was checked after 48 hours and 72 hours in accordance with the criteria (based on "20 diagnostic clinical immunities of contact dermatitis by Shoujirou Nakagawa).

At 48 hours and 72 hours after the affixing, the affixed portion was judged by the naked eye with the results of the degree or irritation as shown in Table 6. The results were scored. The sum of the scores of the respective specimens was divided by the number of subjects and multiplied by 100 to determine the irritation factors, which are shown in Table 7.

TABLE 6

| Judgement on irritation and score of patch test | |
|---|---|
| Irritation judgement | Score |
| No reaction: (−) | 0 |
| Trace of red spots: (±) | 0.5 |
| Clear red spots: (+) | 1.0 |
| Red spots and edema or invasion: (++) | 2.0 |

TABLE 7

| Irritation factor in patch test for silk and talc powder | | |
|---|---|---|
| | After 48 hours | After 72 hours |
| Silk powder | 0 | 0 |
| Talc powder | 10 | 15 |

EXAMPLE 2

The crystalline superfine silk powder of Example 1 was used to check the skin irritation of a lipstick.

The lipstick was prepared with the ratio of ingredients shown in Table 8.

TABLE 8

| Lipstick containing crystalline superfine silk powder | |
|---|---|
| Crystalline superfine silk powder | 20 (%) |
| Bees wax | 5 (%) |
| Candelabra wax | 9 (%) |
| Carnauba wax | 5 (%) |
| Lanolin | 11 (%) |

TABLE 8-continued

| Lipstick containing crystalline superfine silk powder | |
|---|---|
| Castor oil | 25 (%) |
| 2-ethyl hexanoic acid cetyl | 20 (%) |
| Isopropyl myristic acid ester | 4 (%) |
| Glycyrrhiza | 0.5 (%) |
| Tocopherol | 0.5 (%) |

For comparison, a lipstick A, made by maker A, which does not contain silk powder was used.

These lipsticks were used to carry out the same patch test as in Example 1.

The patch test was carried out for 20 people of 14 males and 6 females, ages 26 through 63.

The test results are shown in Table 9.

It was found that the lipstick containing the crystalline superfine silk powder had no skin irritation.

Lipstick A shows skin irritation, however, this is considered to be due to the conventional extender powder contained therein.

TABLE 9

| Irritation factor provided by patch test with lipstick containing crystalline superfine silk powder and lipstick A not containing silk made by maker A | | |
|---|---|---|
| | After 48 hours | After 72 hours |
| Lipstick containing crystalline superfine silk powder | 0 | 0 |
| Lipstick A | 7.5 | 10 |

EXAMPLE 3

Formability of cosmetic powder and crystalline superfine silk powder

To examine the formability of powder, a comparative test was carried out between the crystalline superfine silk powder, and Talc (JA-46R), Mica (No.5500), Titan (A-100), and Kaolin (JP-100), which are used as cosmetic extender powders.

Silk yarn of Eri silkworms was used as a material of the crystalline superfine silk powder and was subjected to the same alkali treatment as in the Manufacturing Example 1 with the composition of Table 10.

The subsequent washing in water, drying, and powdering were carried out in the same manner as in Manufacturing Example 1. The resultant powder had an average particle diameter of 1.7 μm.

The rupture strengths of support beams formed by the powders as raw materials were compared to each other in terms of formability.

Figure 5:
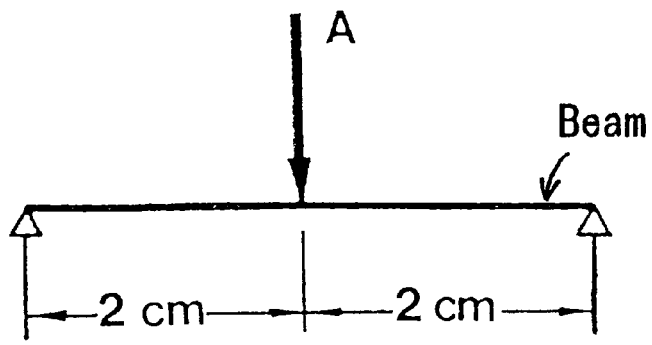
FIG. 5 is a view showing a rupture test of a supporting beam employing powder as a raw material.

In the test, as shown in FIG. 5, a beam was supported at an interval of 4 cm and loaded at point A. The magnitude of the load provided at the time of rupture was measured with Tensilon UTM-II (Toyo Baldwin Co., Ltd.) as the rupture strength.

TABLE 10

| Eri silkworm silk yarn | 20 (g) |
|---|---|
| Sodium carbonate | 8.5 (g) |

TABLE 10-continued

| | |
|---|---|
| Clewat | 4 (g) |
| Hydrosulfite | 2 (g) |
| Water | 400 (g) |

The powders were formed by putting an amount of 2.0 g of each of the powders into a mold of 10 mm (w)_50 mm (L)_30 mm (H) and being subjected to a load of 30 kg/cm².

Figure 6:
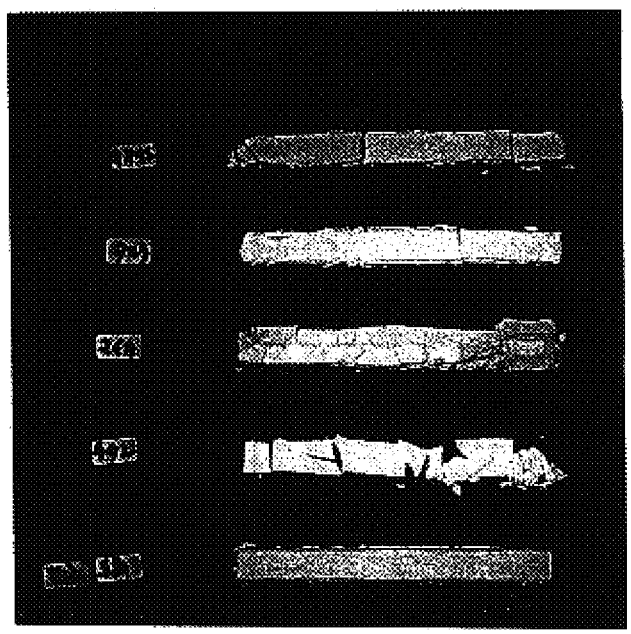
FIG. 6 is a photograph showing the formability of formations obtained from respective powders (talc, mica, titanium, and silk).

FIG. 6 shows formations obtained from each powder. (The photographs showing the formations of talc, mica, titanium, and silk.)

Each of the extender powders has a low formability and is broken in the course of taking the formation out of the mold. The titanium was readily breakable in the direction of the load, while the mica was breakable in the direction parallel to the load.

The kaolin and talc were breakable in both directions.

On the other hand, the crystalline superfine silk powder has good formability and, as a result of the rupture test, was broken at 61.7 g of load.

Thereafter, an amount of 2.0 g of powder, into which 50wt % of silk powder of Manufacturing Example 2 having 2.0 cm in an average particle diameter and 50 wt % of talc (JA-46R) were mixed, was put into the same mold as the above-mentioned and subjected to a load of 30 kg/cm² to be formed. The rupture load was measured to be 30.5 g.

The silk powder can also be used as a molding agent.

COMPARATIVE EXAMPLE 1

Formability of Amorphous Superfine Silk Powder

Raw silk of domestic silkworms was soaked into an aqueous solution 0.05% of carbon acid soda and boiled for 30 minutes with 50 times the bath ratio of raw silk. After having been washed in water, the silk was boiled again in an aqueous solution 0.05% of carbon acid soda (with 50 times the bath ratio of raw silk), then washed in water, and dried.

The percentage of loss in boiling-off was 23.5%.

A liquid having a ratio of calcium chloride: ethyl alcohol: water=1:2:8 (a mole ratio) was used as a dissolving liquid of silk yarn. The silk yarn from which sericin was removed as in the foregoing was dissolved in the dissolving liquid ten times the silk yarn weight (g) at a temperature not more than 80° C.

In the dissolution, the dissolved matter was put into a cellophane tube (semi-transparent film) one hour after the dissolution of the silk yarn was started (the silk yarn was dissolved almost completely in this time), and then alcohol and salt were removed in pure water.

The resultant silk fibroin aqueous solution was freeze-dried.

The resultant silk fibroin was coarsely powdered by means of the rotary impact pulverizer (Sample Mill K-1 made by Fuji Denki Kogyo), and then powdered by means of air-jet pulverizer (Current Jet CJ-10 made by Nisshin Flour Milling Co., Ltd.).

The resultant fine powder is a powder 3 through 5 μm in an average particle diameter and 85% of the powder in weight is amorphous fine silk powder that shows solubility in water at room temperature (20° C.±10° C.). An amount of 2.0 g of this amorphous fine silk powder was put into a mold with 10 mm (W)_50 mm (L)_30 mm (H) and subjected to a load of 30 kg/cm² to be formed.

The formation was fragile and broken in a manner similar to that of mica.

In the case where the rupture test is carried out in the method of Example 3, the rupture test can be carried out with 1 through 4 g of rupture strength.

However, it is difficult to carry out the rupture test with amorphous fine silk powder according to the method of Example 3. By considering Example 4 as a reference, it was found that the amorphous fine silk powder is worse in formability than crystalline superfine silk powder.

EXAMPLE 4

Particle Diameter and Formability of Silk Powder

To examine the formability of crystalline silk powder having different particle diameters, support beams made up of powder were subjected to a rupture test.

First, by using bourette (domestic silkworm silk yarn) as a powder material with the weight of the sodium carbonate of Table 11 being varied within the range from 2.5 through 4.5, the silk yarn was subjected to the alkali treatment, washing in water, drying, and powdering in the same manner as in Manufacturing Example 2.

The average particle diameters of the resultant silk powder were seven types such as 1.2, 1.8, 2.4, 3.2, 5.4, 8.1, and 12.0 μm. These silk powders were used as specimens in the test for formability.

An amount of 2.0 g of each powder was put into a mold with 10 mm (W)_50 mm (L)_30 mm (H) and subjected to loads of 1, 3, 30, 100, 200, and 250 kg/cm² to be formed into beams.

TABLE 11

| | |
|---|---|
| Bourette | 20 (g) |
| Sodium carbonate | 2.5~4.5 (g) |
| Clewat | 4 (g) |
| Hydrosulfite | 2 (g) |
| Water | 400 (g) |

Subsequently, the test, as shown in FIG. 5, a beam was supported at an interval of 4 cm and loaded at point A. A magnitude of the load provided at the time of rupture was measured with Tensilon UTM-II (Toyo Baldwin Co., Ltd.).

The results are shown in Table 12.

In terms of the feeling of touch and formability of powder, and the releasing property of the formed powder, the range available for solid cosmetics lies in A, more preferably, in B in Table 12.

TABLE 12

| Particle diameter (μm) | 1.2 | 1.8 | 2.4 | 3.2 | 5.4 | 8.1 | 12.0 |
|---|---|---|---|---|---|---|---|
| Pressure (kg/cm²) Rupture strength (g) | | | | | | | |
| 1 | 13.3 | 11.7 | 7.1 | - | - | - | - |
| 3 | 38.1 | 34.7 | 31.4 | 14.1 | 6.3 | - | - |
| 30 | 65.5[B] | 54.8 | 49.5 | 25.8 | 15.1 | 7.2 | 4.3 |
| 100 | 150.5 | 175.3 | 95.6 | 62.4 | 36.7 | 11.3 | 9.2 |
| 200 | 293.3 | 285.6 | 186.4 | 138.7[A] | 75.8 | 19.5 | 14.5 |
| 250 | 345.5 | 378.0 | 233.9 | 185.2 | 104.5 | 51.2 | 24.8 |

COMPARATIVE EXAMPLE 2

Silk powder was manufactured according to the method for manufacturing silk fibroin fine powder, which is described in Japanese Laid-Open Patent Publication No. Hei 6-339924.

The average particle diameter was 5.2 μm.

An amount of 2.0 g of this sik powder was put into a mold of 10 mm (W)_50 mm (L)_30 mm (H) and subjected to a load of 100 kg/cm² to be formed into a beam.

The magnitude of the rupture strength of the beam was measured with Tensilon UTM-II as shown in FIG. 5, being found to be 9.4 g.

Based on the fact that the rupture strength of powder 5.4 μm in average particle diameter is 36.7 g at a load of kg/cm² in Table 12, the silk powder of Comparative Example 2 is around a quarter the rupture strength of the silk powder according to the present invention.

The crystalline superfine silk powder of the present invention preserves the original structure of silk yarn. The various properties thereof such as the surface structure, elasticity, and flexibility are not essentially different from those of silk yarn, so that the crystalline superfine silk powder has high formability.

On the other hand, the silk powder of Comparative Example 2 allows the powder particles to turn into an amorphous state in the course of the manufacturing of crystallizing with an alcohol. However, since the silk powder does not maintain the original structure of silk yarn, the silk powder is considered to have low formability.

Silk powder particles having the original structure of silk yarn would show the same birefringence as silk yarn, and observation of the particles under a polarizing microscope using an inspection plate will show particles in yellow or blue. In contrast, the amorphous powder that is crystallized with alcohol shows no birefringence.

Appearance of birefringence in the non-crystalline powder would not show such a high value as that of silk yarn, so that observation by the combination of the shape of the particles and birefringence would substantially show whether the structure provided intrinsically for silk remains in the powder.

Then, in the observation of the silk powder of Comparative Example 2 described above under a polarizing microscope using an inspection plate, 20 through 30% of the particles did not clearly show the same birefringence as that of silk yarn even when the direction of the particles were rotated.

In the case of the crystalline superfine silk powder of the present invention, the particles 1.2 μm in average particle diameter or more, clearly show the same birefringence as that of silk yarn.

Moreover, this powder including many smaller particles of not more than 0.1 μm in diameter, would not show the same birefringence as that of silk yarn.

EXAMPLE 5
Diameter of Silk Powder Particles and Feeling of Friction

The feeling of friction of the crystalline superfine silk powder obtained by powdering silk yarn after the alkali treatment is shown with variations in the mean frictional coefficient (MMD) obtained using the KES apparatus (KES-FB4, a surface property measuring apparatus) made by Kato Tech. Co., Ltd.

The MMD relates to the feeling of roughness that one feels when one rubs the surface of an object. The smaller the MMD, the smoother the surface of the object.

The crystalline superfine silk powder is the same as that of Example 4.

An amount of 8.0 g of each of the powders is put into an aluminum pan 5.7 cm in inner diameter and is subjected to a pressure of 40 kg/cm², at which the releasing property of the formed powder is considered optimum.

For the application of pressure, a Mini press -10 made by Toyo Seiki Co., Ltd. was used.

For measurement of the MMD, the aforementioned aluminum pan was set on the surface property measuring apparatus (KES-FB4).

The friction contact (50 g) in the portion to be brought into contact with the surface of the press formed powder is piano wires of 0.5 mm in diameter, 5 mm in length, 10 pieces arranged in parallel to one another, with the contact area of 5 mm×5 mm.

The friction contact was drawn on the surface of the powder for a distance of 2 cm at a speed of 1 mm/sec in a direction perpendicular to that of the piano wires to measure the frictional tension, while being drawn, with the surface property measuring apparatus. Then, the value of MMD was calculated.

Figure 7:
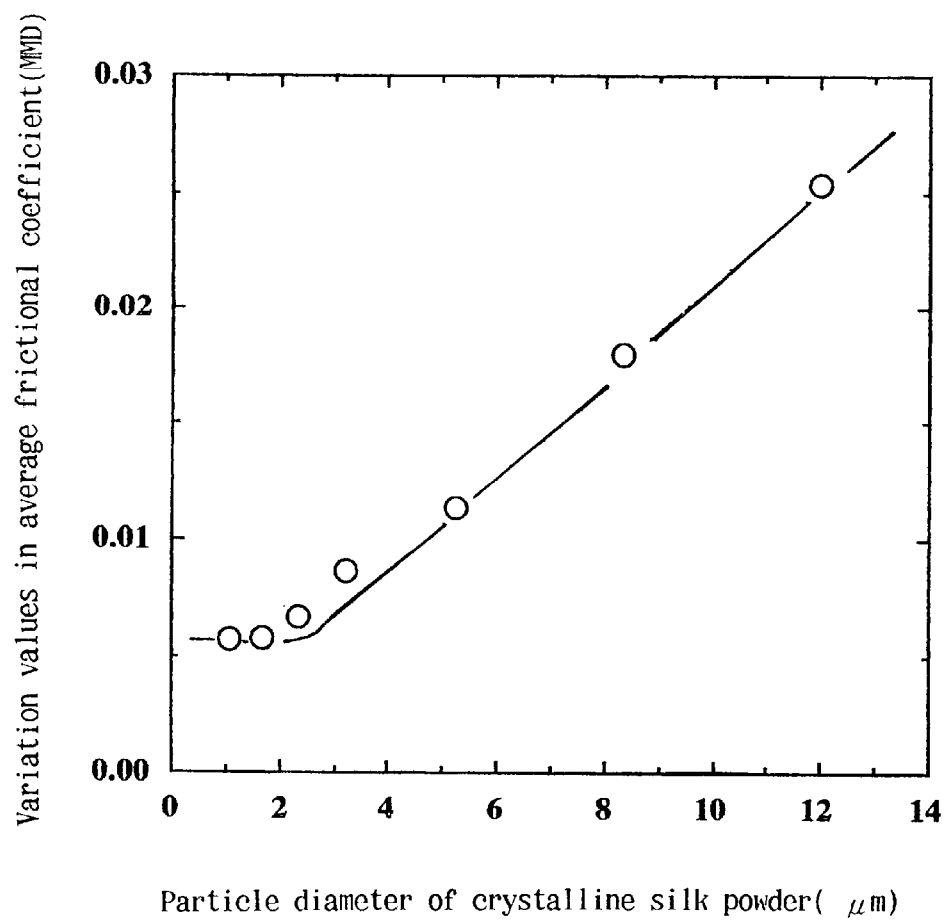
FIG. 7 is view showing the relationship between the size of a crystalline silk powder particle (average particle diameter) and MMD.

The calculated results are shown in FIG. 7.

The MMD suddenly increases with the increasing diameter of particles for those not less than 3 μm in diameter.

On the other hand, as for the particle diameter and feeling of touch of the crystalline superfine silk powder, particles of not more than 6 μm in diameter provide a good feeling of touch, while those not more than 3 μm in diameter provide a very good feeling of touch. Thus, in particular, those below 3 μm in diameter are preferably used as cosmetic powder.

EXAMPLE 6
Dyeing Property of the Crystalline Superfine Silk Powder

First, a dyeing bath of Table 13 was prepared.

The dyeing solution was red.

In the same manner as in Example 1, an amount of 20 g of the silk substance obtained by allowing bourette to be treated with an alkali, wased in water, and dried was soaked in the dyeing bath of Table 13 for one hour at room temperature to be dyed red.

The dyeing solution was red at first and turned transparent one hour later, most of the pigment of Red No. 202 (Tomomi Kasei Co., Ltd.) was dyed to the silk substance.

The silk substance was dried and powdered in the same manner as in Manufacturing Example 2 to obtain colored crystalline superfine silk powder.

TABLE 13

| Dyeing solution | |
| --- | --- |
| Water | 1000 (g) |
| Tartaric acid | 1 (g) |
| Red No.202 | 2 (g) |

The resultant dyed powder was 2.1 μm in average particle diameter. Colors were measured, by means of an automatic spectrophotometer UV-3100S, using (1) the white crystalline superfine silk powder obtained in Manufacturing Example 2 (2.0 μm), (2) dye of Red No.202 (Tomomi Kasei Co., Ltd.), (3) powder dyed red obtained in Example 6 (2.1 μm), and (4) powder into which 50% of the white silk powder of Manufacturing Example 2 and 50% of the red powder obtained by dyeing in Example 6 were mixed.

Figure 8:
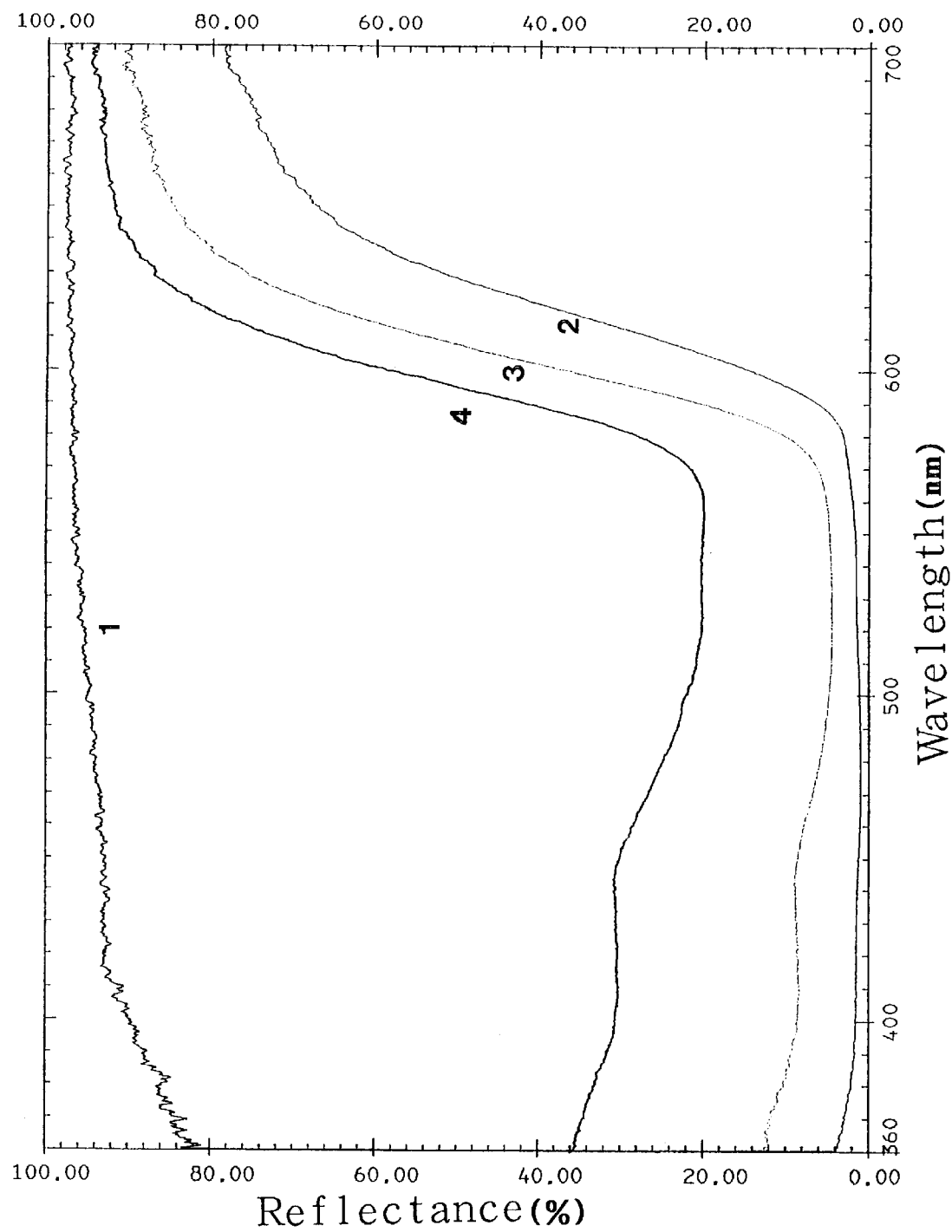
FIG. 8 is a graph showing the curves of reflectance, over wavelengths of 360 through 700 nm, of (1) crystalline superfine silk powder (white), (2) Red No. 202, (3) crystalline superfine silk powder dyed with Red No. 202, and (4) colored crystalline superfine silk powder with 50% of (1) and 50% of (3).

The color of each powder was determined based on the reflectance of wavelengths ranging from 360 through 700 nm (FIG. 8).

Curves (3) and (4) for red have a valley between 500 and 550 nm, while curve (1) is a curve for white, which reflects most visible light.

Curve (4) is closer to curve (3) than the in-between curves (1) and (3). This colored crystalline superfine silk powder has excellent properties as a pigment.

Red No.202 (Tomomi Kasei Co., Ltd.) is a pigment and absorbs the silk substance well.

An amount of 2.0 g of each of the powders (two powders, (3) and (4)) was put into a mold of 10 mm (W)_50 mm (L)_30 mm (H) and subjected to a load of 40 kg/cm² to be press formed. The rupture strength (measured by the same method as in Example 4) of the resultant formation was measured to be in the range of 50 through 100 g.

EXAMPLE 7

Dyeing Property of Crystalline Superfine Silk Powder With a Color Material of Color Cocoons A color material was extracted from the yellow cocoon shell of yellow-white cocoons of domestic cocoons to dye crystalline superfine silk powder. An amount of 20 g of cocoon shells was soaked in an extracting solution of 400 g containing 80% of methyl alcohol and 20% of water (by weight) to extract a color material at a temperature of 65° C. for one hour.

On the other hand, an amount of 5 g of the crystalline superfine silk powder of Manufacturing Example 2 was soaked in each of the aforementioned extracting solutions of 10, 20, 30, 40, 50, 60, and 70 g. Soaking was maintained for 10 hours at temperatures of 20 to 40° C. and the powder was dried.

After having been dried, the powder was powdered by means of a rotary impact pulverizer (Sample Mill KI-1 made by Fuji Denki Kogyo), and then powdered by means of an air-jet pulverizer (Current Jet CJ-10 made by Nisshin Flour Milling Co., Ltd.) into superfine powder.

The resultant crystalline fine silk powder was 2.1 $\mu$m±0.2 $\mu$m in an average particle diameter.

Colors of four points (Table 14) of the crystalline superfine silk powder that had been dyed as described above were measured by means of an automatic spectrophotometer UV-3100S.

Figure 9:
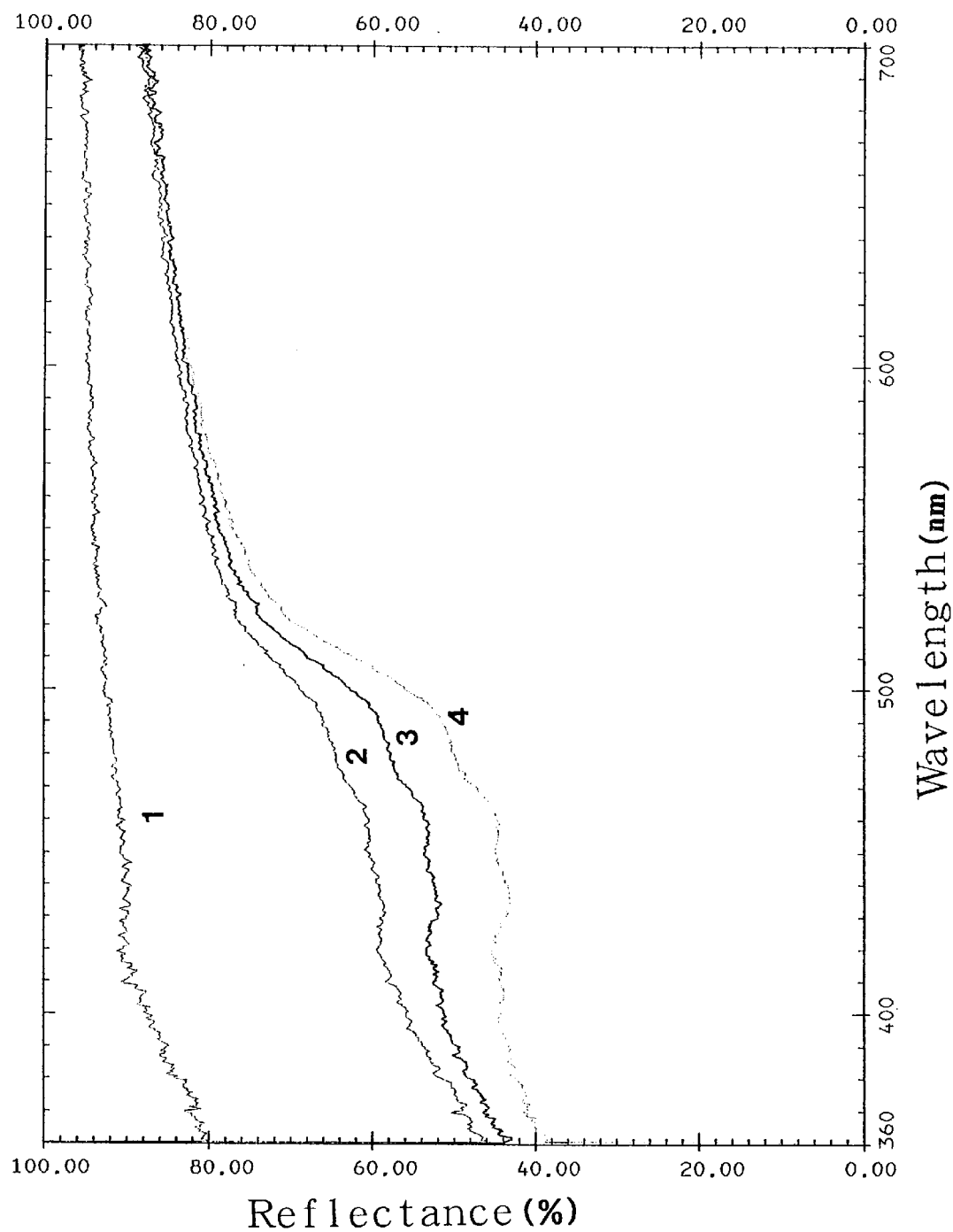
FIG. 9 is a graph showing the curve of reflectance, over wavelengths of 360 through 700 nm, of crystalline superfine silk powder dyed under the condition of Table 14 in Example 7.

The color of each of the dyed powders was determined based on the reflectance (FIG. 9) of wavelengths from 360 through 700 nm.

A patch test was carried out as in Example 1 using the crystalline superfine silk powder dyed as such.

As for results, no skin irritation was found in the 20 subjects.

An amount of 2.0 g of each of the powders (four points of Table 14) was put into a mold of 10 mm (W)_50 mm (L)_30 mm (H) and subjected to a load of 40 kg/cm² to be press formed. The rupture strength (measured by the same method as in Example 3) of the resultant formation was measured to be found in the range of 50 to 100 g.

TABLE 14

Dyeing conditions of crystalline superfine silk powder with a color material extracted from color cocoons

| | Crystalline superfine silk powder (g) | Color material extracting solution (g) |
|---|---|---|
| 1 | 5 | 0 |
| 2 | 5 | 20 |
| 3 | 5 | 40 |
| 4 | 5 | 70 |

INDUSTRIAL APPLICABILITY

The present invention is applied to a cosmetic material that contains crystalline superfine silk powder below 3 $\mu$m in particle diameter and is suitable for the skin. It is also applicable to the field of medicine, as well as to the field of clothing from the common viewpoint of contact with the skin.

What is claimed is:

1. A cosmetic material containing a crystalline superfine silk powder obtained by the steps of:
    bringing a silk substance into contact with an alkali aqueous solution at temperatures ranging from more than 100° C. to 150° C. and a pressure ranging from more than 1 through 5 atmospheric pressures to reduce the tensile strength of the silk substance to not greater than 0.02 g/d without dissolving the silk substance,
    dealkalizing and drying the silk substance, and
    powdering the silk substance into a crystalline powder below 3 $\mu$m in average particle diameter.

2. A cosmetic material according to claim 1, wherein when the silk substance is powdered, an impact powdering and a frictional powdering are combined to powder the silk substance into a crystalline superfine silk powder below 3 $\mu$m in average particle diameter.

3. A cosmetic material according to claim 1, wherein when the silk subtance is powdered, an impact powdering and a frictional powdering are combined to powder the silk substance, which is then classified into a crystalline superfine silk powder below 3 $\mu$m in average particle diameter.

4. A cosmetic material according to claim 2, wherein when powdering is carried out by a combination of the impact powdering and the frictional powdering, the dried silk substance is powdered into a silk powder 4 to 15 $\mu$m in average particle diameter through impact powdering—frictional powdering and fricitional powdering—impact powdering, or frictional powdering—impact powdering—fricitonal powdering in sequence, and then impact powdering is carried out to obtain a crystalline superfine silk powder below 3 $\mu$m in average particle diameter.

5. A cosmetic material containing a colored crystalline superfine silk powder obtained by the steps of:
    bringing a silk substance into contact with an alkali aqueous solution at a temperature ranging from more than 100° C. to 150° C. and a pressure ranging from more than 1 through 5 atmospheric pressures to reduce the tensile strength of the silk substance to not greater than 0.02 g/d,
    dealkalizing and drying the silk substance,
    powdering the silk substance into a crystalline superfine silk powder below 3 $\mu$m in average particle diameter, and either
    dyeing said crystalline superfine silk powder with a natural or synthetic coloring material or mixing said crystalline superfine silk powder with a natural or synthetic coloring material.

6. A cosmetic material containing a crystalline superfine silk powder obtained by the steps of:
    bringing a silk substance into contact with an alkali aqueous solution at a temperature ranging from more than 100° C. to 150° C. and a pressure ranging from more than 1 through 5 atmospheric pressures to reduce the tensile strength of the silk substance to not greater than 0.02 g/d,
    dealkalizing and washing the silk substance in water,
    dyeing the silk substance with a natural or synthetic coloring material, and
    powdering the silk substance into a crystalline superfine silk powder below 3 $\mu$m in average particle diameter.

7. A method of preparing crystalline superfine silk powder having an average particle diameter less than 3 $\mu$m, comprising the steps of:
    contacting a silk substance with an alkali aqueous solution at a temperature of more than 100° C. and a pressure of more than one atmosphere to reduce the tensile strength of the silk substance to no greater than 0.02 g/d without dissolving the silk substance;

dealkalizing the silk substance having the reduced tensile strength;

drying the dealkalized silk substance; and powdering the dried silk substance to obtain crystalline superfine silk powder having an average particle diameter less than 3 μm.

8. The method of claim 7, wherein the tensile strength of the silk substance is no greater than 0.01 g/d.

9. A method of preparing a cosmetic material containing a colored crystalline superfine silk powder having an average particle diameter less than 3 μm, comprising the steps of:

contacting a silk substance with an alkali aqueous solution at a temperature of from more than 100° C. to 150° C. and a pressure ranging from more than 1 through 5 atmospheres to reduce the tensile strength of the silk substance to no greater than 0.02 g/d;

dealkalizing the silk substance having the reduced tensile strength;

drying the dealkalized silk substance;

powdering the dried silk substance to obtain crystalline superfine silk powder having an average particle diameter less than 3 μm; and either dyeing the crystalline superfine silk powder with a natural or synthetic coloring material or mixing the crystalline superfine silk powder with a natural or synthetic coloring material.

10. A method of preparing a cosmetic material containing a crystalline superfine silk powder having an average particle diameter less than 3 μm, comprising the steps of:

contacting a silk substance with an alkali aqueous solution at a temperature of from more than 100° C. to 150° C. and a pressure ranging from more than 1 through 5 atmospheres to reduce the tensile strength of the silk substance to no greater than 0.02 g/d;

dealkalizing and washing the silk substance in water;

drying the silk substance;

dyeing the silk substance with a natural or synthetic coloring material; and powdering the silk substance into a crystalline superfine silk powder having an average particle diameter than than 3 μm.

11. A cosmetic material containing a crystalline-superfine silk powder obtained by the steps consisting essentially of:

bringing a silk substance into contact with an alkali aqueous solution at temperatures ranging from more than 100° C. to 150° C. and a pressure ranging from more than 1 through 5 atmospheric pressures to reduce the tensile strength of the silk substance to not greater than 0.02 g/d without dissolving the silk substance;

dealkalizing and drying the silk substance; and powdering the silk substance into a crystalline powder below 3 μm in average particle diameter.

12. A method of preparing crystalline superfine silk powder having an average particle diameter less than 3 μm, consisting essentially of the steps of:

contacting a silk substance with an alkali aqueous solution at a temperature of more than 100° C. and a pressure of more than one atmosphere to reduce the tensile strength of the silk substance to no greater than 0.02 g/d without dissolving the silk substance;

dealkalizing the silk substance having the reduced tensile strength;

drying the dealkalized silk substance; and powdering the dried silk substance to obtain crystalline superfine silk powder having an average particle diameter less than 3 μm.

* * * * *